United States Patent
Quach

Patent Number: 5,083,919
Date of Patent: Jan. 28, 1992

[54] RETAINER AND METHOD OF MAKING

[76] Inventor: Thanh D. Quach, 5311 Weymouth Dr., Springfield, Va. 22151

[21] Appl. No.: 672,829

[22] Filed: Mar. 21, 1991

[51] Int. Cl.⁵ .............................................. A61C 3/00
[52] U.S. Cl. ............................................ 433/6; 433/24
[58] Field of Search ................ 433/6, 24, 2; 128/861, 128/862

[56] References Cited

U.S. PATENT DOCUMENTS

| | | | |
|---|---|---|---|
| 3,994,068 | 11/1976 | Goshgarian | 433/6 |
| 4,195,046 | 3/1980 | Kesling | 433/6 |
| 4,299,568 | 11/1981 | Crowley | 433/6 |

Primary Examiner—John J. Wilson
Assistant Examiner—Cindy A. Cherichetti
Attorney, Agent, or Firm—James C. Wray

[57] ABSTRACT

A Hawley-type retainer is formed with a reinforcing design carrier laminated within a colored plastic retainer body and partially surrounded by a clear or colored plastic mound, which is laminated within the colored plastic body. The clear or colored and highly visible design on the carrier adds interest and identification to the retainer, promoting its use and location and preventing loss or accidental destruction. The invention is attractive to children so they wear the retainer often.

9 Claims, 3 Drawing Sheets

RETAINER AND METHOD OF MAKING

BACKGROUND OF THE INVENTION

This invention concerns the construction of retainers with embedded designs on carriers.

Retainers are widely used by orthodontic patients to maintain teeth alignment after the removal of fixed appliances.

Retainers are usually removed and cleaned periodically and may be removed at mealtimes. Some retainers are used primarily during sleep.

One of the most popular forms of retainer is a Hawley retainer, which has a labial wire having ends embedded in a plastic palatal plate. The plastic palatal plate has a central body portion made in a compound dish-like curve with a curved rearward edge and serrated lateral and frontal edges, with points which fit partially between teeth to hold the plate and the retainer in perfect alignment.

The labial wire usually extends outward from points on the edges of the plate through spaces between molars and cuspids, and arches around the cuspids and extends tightly anteriorly around the frontal teeth or incisors.

Anchor wires extend outward from the retainer body through lateral edge points which extend between molars.

The maxillary Hawley retainer used with the upper teeth has a central crowned plate which matches the curve of the hard, bony forward part of the palate or the roof of the mouth.

The tissue-side surface of the retainer body is formed in a cavity in a mold created as a positive from a negative impression taken from the patient's anatomical mouth features. The surface of the retainer which lies against the palate of the mold is left unfinished. The unfinished nature of that surface bears against the soft tissue covering the hard, bony frontal palate of the wearer and aids in the preventing of slipping. The tongue-side exposed surface of the retainer is polished smooth, because the tongue does not readily accommodate to surface irregularities.

One of the long-standing problems of retainers is that they are often made of clear or colored plastic with highly visible wires, and are made in such a shape that their configuration and appearance is unattractive so that retainers often fall into disuse. Clear or colored retainers may be difficult to see, and lost retainers are a constant and recurrent problem.

A need exists for a system to encourage the use of retainers and to help locate retainers.

SUMMARY OF THE INVENTION

The present invention encourages the use of retainers by making the retainers bright, personalized, attractive devices. An embedded three dimensional design and carrier become part of the identification of the retainer, which identifies the retainer with a particular user. The bright, attractive design encourages a user to keep the retainer in the open as a reminder to use the retainer. The bright designs call attention to the retainer when it is out of the mouth, so that a person will be able to locate the retainer and will be reminded of the beneficial qualities of using the retainer.

In creating the present invention the inventor, who is a skilled orthodontic appliance creator, saw the need for encouraging the display and use by promoting an attractiveness of retainers, and promoting their personal identification with personally selected designs.

In making the invention, the inventor first conceived of molding individual three dimensional design pieces out of the same plastic material from which the retainer bodies are made, and then molding the premolded pieces into the body of the retainer.

As a second step, the inventor used shapes from preformed paper-thin aluminum sheets.

Finally, the inventor discovered that designs printed on cloth fabric cotton which are incorporated into the retainers ar highly suited to the present invention.

The inventor then found that the designs were obscured and rendered less attractive by the overlaying of the designs with colored plastic. The inventor was still not fully satisfied with his invention.

Finally, the inventor created built up mounds of clear or colored plastic over the designs and surrounded the mounds with colored plastic buildups and a fine, thin layer of colored plastic to tie the design mound and the colored plastic body together.

The results were a highly unusual, novel and unobvious colored retainer with a clear or colored, sharp, personalized design. The preferred design carrier material is a fabric cotton, having a cotton or cotton and polyester blend. A thin woven material with a colorfast printed design on one side is preferred.

Other carrier materials may be used. Metal foil, thin plastic compatible with the plastic of the retainer, and paper are suitable.

The cloth material or metal is preferred because it is believed to strengthen the retainer while adding the personalized design.

The strength and the design are imparted to the retainer without adding substantial material, weight or thickness.

The metal, plastic and paper laminations also provide laminar structures which increase the strength without increasing weight or thickness. The paper provides fibers which may increase the strength of the appliance.

The invention is useful in orthodontic appliances and orthopedic appliances, including Hawley retainers, anterior spring retainers, Template Mandibular Joint (TMJ) splints, bionator, biofinisher, orthopedic corrector, Schwarz, Schwarz fangear, Nord cross bit, sagittal, sagittal-Schwarz (3 way), Jackson and Frankel appliances.

A preferred Hawley-type retainer is formed with a reinforcing design carrier laminated within a colored plastic retainer body and partially surrounded by a clear or colored liquid monomer plastic mound, which is laminated integrally within the colored plastic body. The design carrier adds interest, personal uniqueness and identification to the retainer, promoting its use and location and preventing loss or accidental destruction.

Preferably a Hawley retainer has a three dimensional design element embedded in the retainer. The retainer has a rigid palatal body uniformly constructed of one integral plastic molded piece having a curved rearward edge and curved lateral and frontal edges with points for projecting between teeth of a wearer. A labial arch wire is embedded in the body and extends from forward portions of lateral edges outward beyond the front edge for overlying frontal incisor teeth of a wearer. The body portion has a raised central palate-contacting portion and a three-dimensional, flexible design embedded in the central portion and visible through upper and lower surfaces of the body.

The preferred three-dimensional carrier has a design imprinted on a woven cloth fabric and particularly a design imprinted on one side of a fabric. The design is printed on paper, or on metal, plastic, fabric or paper.

The preferred method of making a Hawley retainer comprises flowing liquid plastic material over a mold cavity base, placing a three-dimensional design on the liquid plastic material and placing a labial wire in the liquid plastic material. Clear or colored liquid plastic material is flowed over the design and copolymer powdered material is added in a mound on top of the design. Clear or colored liquid is flowed over the mound. Colored liquid plastic monomer material is flowed over the mold in the palatal area and partially into spaces between teeth. Co-polymer powder is distributed over the colored liquid plastic material. Colored liquid monomer is flowed over the powder, and the resulting polymer is allowed to gel to a tacky state. The retainer is submerged in water in a closed container, and the container is heated and pressurized to about 120° F. at about 20 psig for about 15 minutes until the polymer is fully polymerized and hardened. Then an inner surface of the polymer body is polished.

The preferred building up of a mound on top of the design is achieved by covering the design with a clear or colored monomer liquid, adding co-polymer powder, and flowing clear or colored plastic monomer liquid over the co-polymer powder.

Preferably the monomer is an ester of the formula $C_5H_8O_2$, such as methylmethacrylate with 0.01% pigment, 0.75% catalyst, 2% additives and 5% butandioldimethacrylate. The preferred powder is a co-polymer based on polymethylmethacrylate with a molecular weight $1.54-10^6$, a peroxide content of 0.4-0.6%, and a central bead size of 63-90 my.

Preferably co-polymer powder is distributed over the second liquid layer and over a colored liquid layer over the remainder of the body, and all of the co-polymer powder is covered with a colored liquid layer A very thin layer of liquid and powder is first flowed over the entire mold cavity surface before placing the design on a carrier in the center of the mold cavity.

These and further and other objects and features of the invention are apparent in the disclosure, which includes the above and ongoing written specification, with the claims and the drawings.

DETAILED DESCRIPTION OF THE DRAWINGS

Figure 1:
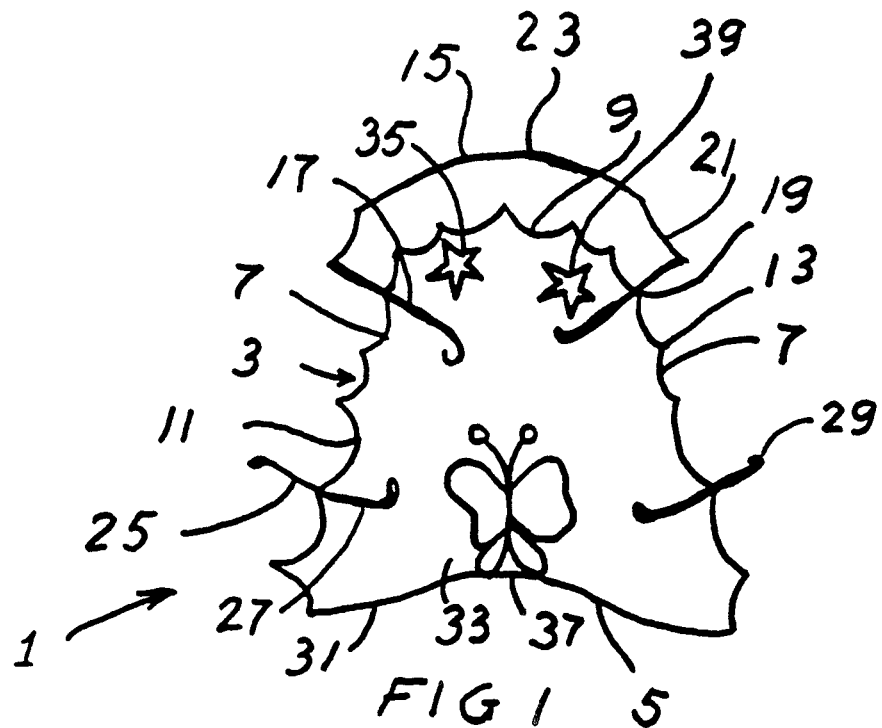
FIG. 1 is a top view of the retainer of the present invention.
Figure 2:
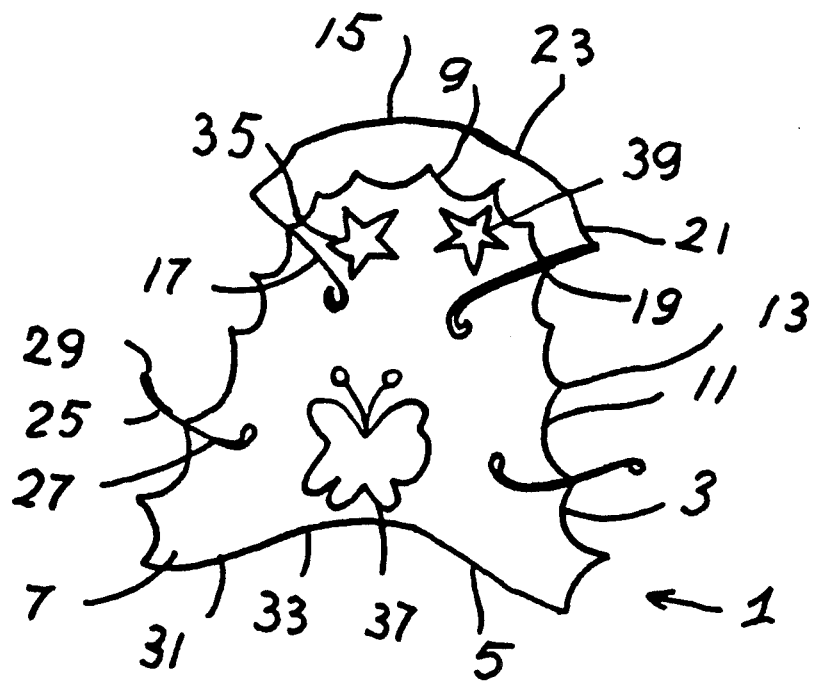
FIG. 2 is a bottom view of the retainer of the present invention.
Figure 3:
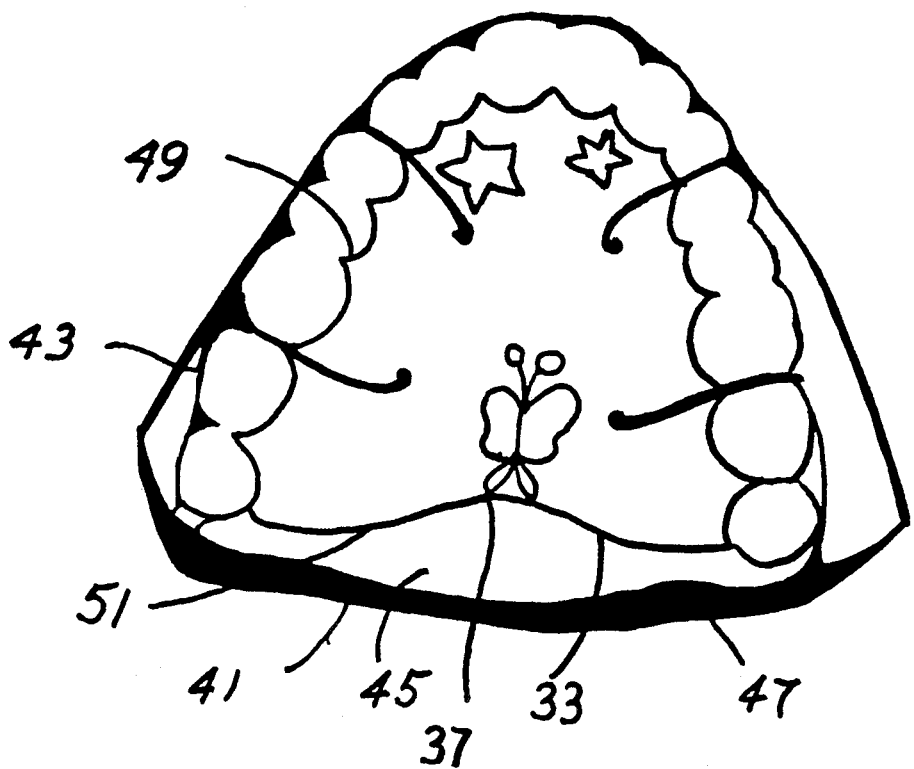
FIG. 3 is a view of the retainer positioned in a mold which is a positive made of a negative of the maxillary arch, teeth and palate of a retainer user.

Referring to FIG. 1, the retainer of the present invention is generally indicated by the numeral 1. The retainer has a main body 3 formed of a palatal arch portion 5, lateral portions 7 and a frontal portion 9. The frontal portion and the lateral portions are bound by serrated edges 11 with points 13, which extend between adjacent teeth to hold the retainer aligned in the maxillary arch or the roof of the mouth. A labial arch wire 15 has opposite ends 17 embedded in the retainer body 5. The labial arch wire extends through points 19 between teeth, usually between a cuspid and an adjacent bicuspid, and forms an arch 21 which fits upward and around a cuspid, and then a labial arch 23 which tightly holds the front anterior incisor teeth in alignment. Anchor wires 25 have inner ends 27 integrally molded within the retainer body 5. Outer ends 29 are bent upward and enlarged to fit in spaces between adjacent molars. The retainer has a curved rearward edge 31, which is posterior of the usual posterior excursion of the tongue so that nerve endings on the tongue are not continually aware of the edge.

The body of the retainer is formed with a clear or colored methacrylate plastic which is constructed of a liquid methylmethacrylate monomer and a co-polymer powder. The monomer and co-polymer dry to a tack-free state in air and are heated under pressure in the mold cavity to complete polymerization. In a preferred embodiment of the invention, the polymeric material incorporates one or more design carriers 33 and 35 which have designs 37 and 39, in this case a butterfly and stars. In construction, the labial arch wires are formed according to the positive mold and are placed in the positive mold with ends extending into the cavity. The positive mold 41 is formed from a negative impression taken from the patient, with individual teeth 43 and the roof arch 45. Fluent material in the form of liquid and then powder and then liquid is laid in the cavity 47 formed by the roof arch and in interstitial spaces 49, which project outward between adjacent teeth. First a layer of liquid is spread over the entire cavity 47, extending it into the spaces 49. The thin liquid migrates under the wires, between the wires and the cavity. Then a thin layer of powder is uniformly spread across the liquid. The powder dissolves in the liquid and migrates between the wires and cavity. Then a design carrier 33 is placed in the cavity in the desired position so that the design 37 faces in the correct direction. Next a mound of clear or colored plastic is built over the designed carrier by first flowing a clear or colored monomer liquid completely over the carrier, and then distributing a relatively thick layer of co-polymer powder over the liquid and flowing further clear or colored liquid over the powder. The powder and liquid dissolve into a thixotropic mass. Then additional liquid is flowed around the mound 51 by manipulating and reorienting the mold 41 to flow the liquid around the mold cavity as desired. Then a layer of powder is applied to the liquid, and finally a layer of colored liquid is applied over the powder and over the mound 51 which covers the design.

The entire mold is then partially polymerized and air dried and is then submerged in water in a closed pressurized container and held at about 120° F. at about 20 psi for about 15 minutes. The retainer is then removed from the cavity. The tissue-side surface is left in its molded condition and the tongue-side surface is finished and trimmed with a burr, polished with pumice and smoothed.

Figure 4:
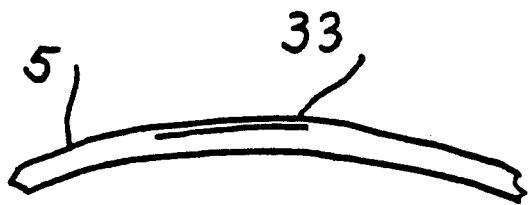
FIG. 4 is a detail of the design within the retainer.

As shown in FIG. 4, the design carrier 33 is embedded within the body 5 of the retainer.

Figure 5:
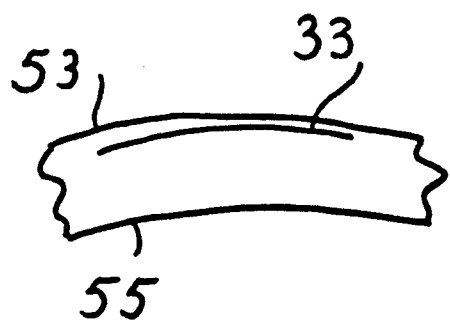
FIG. 5 is an enlarged detail of the design within clear or colored plastic within the colored retainer body.

FIG. 5 shows an area of the retainer in greater detail, showing the carrier 33 close to the upper surface 53 of the retainer and spaced from the lower surface 55.

Figure 6:
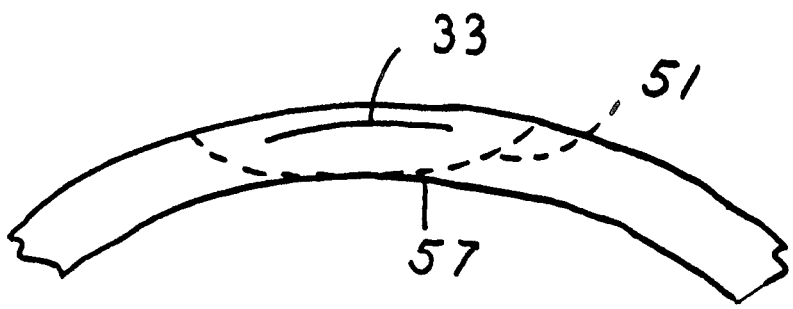
FIG. 6 is a schematic representation of the design within clear or colored plastic within the colored retainer body.

FIG. 6 schematically shows the mound 51 of clear or colored plastic which substantially extends around the carrier 33. A thin layer 57 of colored plastic is formed over the mound in a preferred embodiment.

Figure 7:
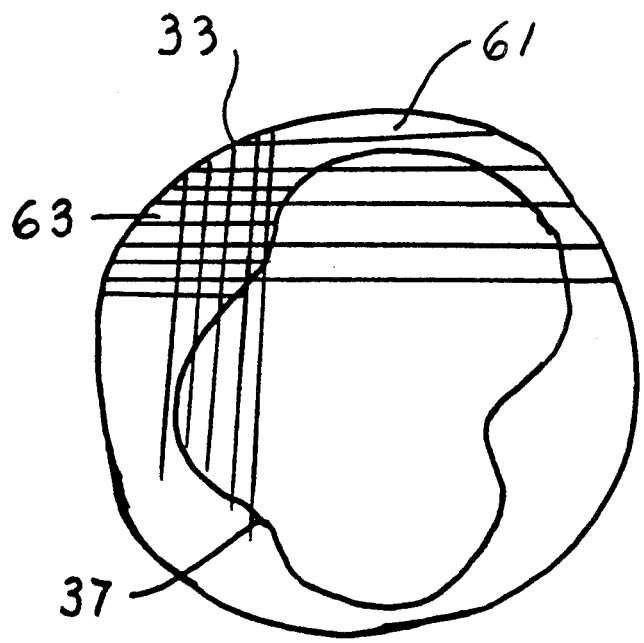
FIG. 7 is a detail of a preferred design carrier.

FIG. 7 shows a preferred carrier 33 with woven threads 61 and 63, and the design 37 printed on one surface.

In one preferred form of the invention, labial arch and clasp wires are placed in the mold and liquid monomer is spread in a thin layer in the design-receiving area of the base of the mold cavity. A thin layer of co-polymer powder is spread over the liquid. The design carrier is placed over the gel formed by the powder on the liquid. The whole cavity is covered with powder and colored liquid is spread over the powder, working step by step and area by area to prevent migration of the gel. The tacky-surface gel is immersed in water and heated under pressure to complete polymerization and hardening.

In another preferred form of the invention, the wires are placed in the mold and the whole mold cavity is coated with a thin layer of liquid, then a thin layer of powder, and then a thin layer of liquid over the powder in the design area. The design carrier is positioned on the gel formed by the liquid-powder-liquid application in the design-receiving area. If the design is on a metal carrier, the carrier is covered with powder first. Then if a clear mound is desired, clear liquid is placed over the powder. Then powder is distributed over the entire cavity and liquid is placed over small areas of the powder in sequences to prevent migration of the resulting gel.

A Hawley-type retainer is formed with a reinforcing design carrier laminated within a colored plastic retainer body and partially surrounded by a clear or colored plastic mound, which is laminated within the colored plastic body. The clear or colored and highly visible design on the carrier adds interest and identification to the retainer, promoting its use and location and preventing loss or accidental destruction.

While the invention has been described with reference to specific embodiments, modifications and variations of the invention may be constructed without departing from the scope of the invention, which is defined in the following claims.

I claim:

1. A Hawley retainer having a three dimensional design element embedded in the retainer, comprising a rigid palatal body uniformly constructed of one integral plastic molded piece having a curved rearward edge and curved serrated lateral and frontal edges with points for projecting between teeth of a wearer, and having a labial arch wire embedded in the body and extending from points on forward portions of lateral edges through cuspid-bicuspid spaces and outward beyond the front edge for overlying frontal incisor teeth of a wearer, the rigid palatal body portion having a raised central palate-contacting portion and having a three-dimensional, flexible design embedded in the central portion and visible through tissue-side and tongue-side surfaces of the body, wherein the three-dimensional design is imprinted on a woven cloth fabric.

2. The apparatus of claim 11. wherein the three-dimensional design includes a design imprinted on one side of a fabric.

3. A Hawley retainer having a three dimensional design element embedded in the retainer, comprising a rigid palatal body uniformly constructed of one integral plastic molded piece having a curved rearward edge and curved serrated lateral and frontal edges with points for projecting between teeth of a wearer, and having a labial arch wire embedded in the body and extending from points on forward portions of lateral edges through cuspid-bicuspid spaces and outward beyond the front edge for overlying frontal incisor teeth for a wearer, the rigid palatal body portion having a raised central palate-contacting portion and having a three-dimensional, flexible design embedded in the central portion and visible through tissue-side and tongue-side surfaces of the body, wherein the design is printed on paper.

4. A Hawley retainer having a three dimensional design element embedded in the retainer, comprising a rigid palatal body uniformly constructed of one integral plastic molded piece having a curved rearward edge and curved serrated lateral and frontal edges with points for projecting between teeth of a wearer, and having a labial arch wire embedded in the body and extending from points on forward portions of lateral edges through cuspid-bicuspid spaces and outward beyond the front edge for overlying frontal incisor teeth of a wearer, the rigid palatal body portion having a raised central palate-contacting portion and having a three-dimensional, flexible design embedded in the central portion and visible through tissue-side and tongue-side surfaces of the body, wherein the design is printed on a design carrier consisting of metal, plastic, fabric or paper.

5. The method of making an orthopedic/orthodontic appliance, comprising placing ends of labial and clasp wires in a base of a mold, flowing colored liquid plastic monomer material over a base of a mold cavity, covering the liquid monomer with a thin layer of co-polymer powder, placing a three-dimensional design carrier on the plastic, flowing liquid plastic monomer material over the design, adding co-polymer powdered material in a mound on top of the design, flowing colored liquid plastic material over the mold in the palatal area and partially into spaces between teeth, distributing co-polymer powder over the colored liquid plastic material, flowing liquid monomer and allowing the polymer to dry to a tack-free state, submerging the retainer in water in a closed container and heating and pressurizing the container to about 120° F. at about 20 psig for about 15 minutes until the polymer is fully polymerized, and then polishing a concave inner surface of the polymer.

6. The method of claim 5, wherein the building up of a mound on top of the design comprises covering the design with a liquid monomer, adding co-polymer powder, and flowing clear or colored plastic monomer liquid over the co-polymer powder.

7. The method of claim 6, further comprising distributing co-polymer powder over the second liquid layer and over a colored liquid layer over the remainder of the body, and covering all of the co-polymer powder with a colored liquid layer.

8. The method of claim 5, wherein the first flowing of liquid comprises flowing a very thin layer of liquid and powder over the entire mold cavity surface before placing the design carrier in the center of the mold cavity.

9. The method of claim 5, wherein the appliance is a Hawley retainer.

* * * * *